US006987136B2

(12) United States Patent
Erbe et al.

(10) Patent No.: US 6,987,136 B2
(45) Date of Patent: Jan. 17, 2006

(54) BIOACTIVE SPINAL IMPLANT MATERIAL AND METHOD OF MANUFACTURE THEREOF

(75) Inventors: Erik M. Erbe, Berwyn, PA (US); James P. Murphy, Broomall, PA (US); Gregory J. Pomrink, Lansdale, PA (US)

(73) Assignee: Vita Special Purpose Corporation, Wilmington, DE (US)

( * ) Notice: Subject to any disclaimer, the term of this patent is extended or adjusted under 35 U.S.C. 154(b) by 0 days.

(21) Appl. No.: 10/127,947

(22) Filed: Apr. 23, 2002

(65) Prior Publication Data

US 2003/0087984 A1 May 8, 2003

Related U.S. Application Data

(60) Provisional application No. 60/339,871, filed on Dec. 12, 2001, and provisional application No. 60/305,070, filed on Jul. 13, 2001.

(51) Int. Cl.
   *A61F 2/28* (2006.01)
   *C08K 3/34* (2006.01)
   *C08K 3/40* (2006.01)

(52) U.S. Cl. ............... 523/114; 523/113; 523/115; 524/456; 524/492; 424/423; 501/72

(58) Field of Classification Search .......... 523/113, 523/114, 115; 524/456, 492; 424/423; 501/72
   See application file for complete search history.

(56) References Cited

U.S. PATENT DOCUMENTS

| 4,110,184 A | 8/1978 | Dart et al. ............ 204/159.23 |
| 4,491,453 A | 1/1985 | Kobiltz et al. ............... 433/217 |
| 4,698,373 A | 10/1987 | Tateosian et al. ............. 522/95 |
| 4,801,528 A | 1/1989 | Bennett ....................... 433/220 |
| 5,024,232 A | 6/1991 | Smid et al. ................. 128/654 |
| 5,415,546 A | 5/1995 | Cox, Sr. ..................... 433/213 |
| 5,681,742 A | 10/1997 | MersKelly et al. ...... 435/288.1 |
| 5,681,872 A | 10/1997 | Erbe .......................... 523/114 |
| 5,914,356 A | 6/1999 | Erbe .......................... 523/114 |
| 6,039,762 A | 3/2000 | McKay ........................ 623/17 |
| 6,123,731 A | 9/2000 | Boyce et al. ............ 623/23.63 |
| 6,132,465 A | 10/2000 | Ray et al. ............... 623/17.16 |
| 6,261,586 B1 | 7/2001 | McKay ....................... 424/423 |

OTHER PUBLICATIONS

John W. Brantigan, MD., "Compression strength of donor bone for posterior lumbar interbody fusion", *Spine*, 1993, 18, 1213–1221.

Pattin, C.A. et al., "Cyclic mechanical property degradation during fatigue loading of cortical bone", *J. Biomechanics*, 1996, 29(1), 69–79.

Zioupos, P., et al., "Experimental and theoretical quantification of the development of damage in fatigue tests of bone and antler", 1996, 29(8), 989–1002.

*Primary Examiner*—Tae H. Yoon
(74) *Attorney, Agent, or Firm*—Woodcock Washburn LLP

(57) ABSTRACT

Bioactive spinal implant materials having optimized radiopacity, stiffness, and bioactivity properties for formulation of shaped bodies capable of withstanding large dynamic, compressive loads are provided. The invention also provides methods of making the optimized implant materials.

21 Claims, 12 Drawing Sheets

(5 of 12 Drawing Sheet(s) Filed in Color)

Human
Allograft
Bone
(left side)

Present
Invention
(right side)

Human
Allograft
Bone (left side)

Present
Invention (right side)

1=Bovine Tibial Bone
2=Carbon Fiber Cage
3=Example of Cage with
Present Invention Material
4=Titanium Hip Stem
5=Metallic Vertebral Implant
6=Example of Cage with
Present Invention Material
(having radiopacity different from
the present invention material
used for cage in 3)

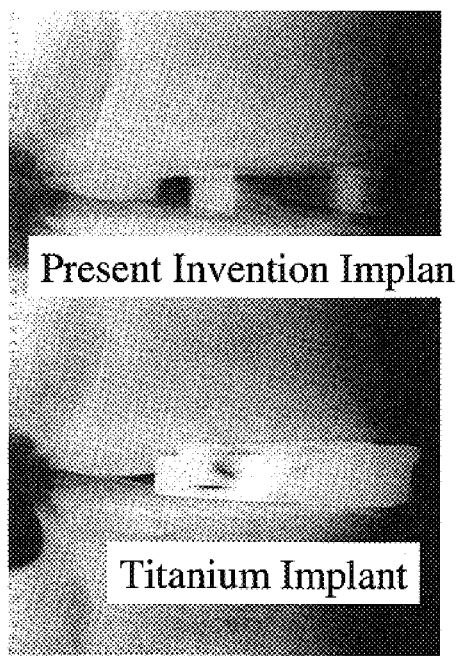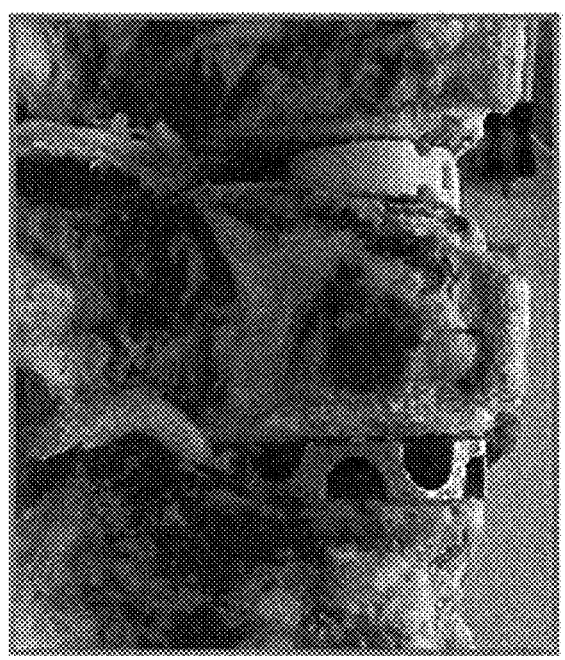
FIGURE 2b
FIGURE 2c

BIOACTIVE SPINAL IMPLANT MATERIAL AND METHOD OF MANUFACTURE THEREOF

CROSS-REFERENCE TO RELATED APPLICATIONS

This application claims priority to Provisional Application Ser. No. 60/339,871, filed Dec. 12, 2001, and Provisional Application Ser. No. 60/305,070, filed Jul. 13, 2001.

FIELD OF THE INVENTION

The present invention relates to spinal implant materials having optimized radiopacity, stiffness, and bioactivity properties and to methods of making such optimized spinal implant materials. The materials of the present invention can be used in a variety of orthopaedic applications, such as cervical fusion, anterior lumbar interbody fusion (ALIF) or posterior lumbar interbody fusion (PLIF). They may be implanted between adjacent vertebrae to treat or prevent back pain in patients with conditions such as degenerative disc disease.

BACKGROUND OF THE INVENTION

Lower back and neck pain is oftentimes attributed to the rupture or degeneration of intervertebral discs due to degenerative disk disease, spondylolisthesis, deformative disorders, trauma, tumors, and the like. This pain typically results from the compression of spinal nerve roots by damaged discs between the vertebra, the collapse of the disc, or the resulting adverse effects of bearing the patient's body weight through a damaged unstable vertebral joint. To remedy this, spinal implants have been inserted between the vertebral bodies to restore the joint to its previous height and stabilize the motion at that spinal segment.

Surgical treatments to restore the vertebral height typically involve excision of the ruptured soft disc between the vertebrae, often with subsequent insertion of a spinal implant or interbody fusion device to fuse and stabilize the segment.

Spinal implants or interbody fusion devices have been used to fuse adjacent vertebral bodies since the 1960's. U.S. Pat. No. 6,261,586 to McKay and U.S. Pat. No. 6,123,731 to Boyce, et al. disclose spinal implant devices that are comprised of allograft materials. One major drawback associated with allograft devices is the risk of disease transmission. Further, since companies that provide allograft implants obtain their supply from donor tissue banks, there tend to be limitations on supply. Current synthetic devices, which are predominantly comprised of metals such as titanium, also present drawbacks. For instance, the appearance of metal spinal implants on x-ray tends to have an artificial fuzziness that makes assessment of fusion, which is one of the clinical criteria of a successful interbody fusion device, very difficult. Moreover, synthetic materials of this type tend to have mechanical properties that are unevenly matched to bone.

U.S. Pat. Nos. 5,681,872 and 5,914,356 to Erbe teach bioactive load bearing bone bonding compositions having a modulus of elasticity between 5 GPa to 50 GPa and added components that impart radiopacity. Erbe further teaches that the moduli of these compositions are closer to those of natural bone (7 GPa to 20 GPa) than PMMA alone (3 GPa to 5 GPa) or metal (100 GPa to 200 GPa). Erbe does not provide guidance as to a radiopacity range optimal for implants.

U.S. Pat. No. 6,261,586 to McKay teaches a composition of natural selectively deactivated bone mineral, which has a modulus of elasticity similar to the surrounding bone, as well as an approximate radiopacity of the bones of the vertebrae. McKay also discloses that commonly used implant materials have stiffness values far in excess of bone. The stiffness of cortical bone is 17 GPa. For instance, the stiffness of titanium alloy is 114 GPa, and the stiffness of 316L stainless steel is 193 GPa. Yet, there has been no showing of a synthetic material with a stiffness equivalent to bone.

U.S. Pat. No. 6,039,762 to McKay teaches a reinforced bone graft substitute in the form of an interbody fusion spacer composed of a porous, biocompatible ceramic material having a compressive strength of only at least 7 MPa and most preferably of only at least 40 MPa, and having the radiopacity of natural bone. U.S. Pat. No. 6,123,731 to Boyce, et al. teaches an osteoimplant fabricated from a solid aggregate of bone-derived elements having a compression strength between 10 MPa to 200 MPa and an added component that has the possibility of imparting radiopacity. U.S. Pat. No. 5,415,546 to Cox, Sr. teaches a radiopaque dental composition containing from about 10% to 80% of a radiopaque material such as diatrizoate sodium, barium sulfate, iodine or barium material. However, there has been no disclosure of a material with both mechanical properties similar to bone and an equivalent radiopacity of bone.

U.S. Pat. No. 5,024,232 to Smid teaches radiopaque heavy metal polymer complexes that have radiopacities equivalent to that of aluminum or higher. Again there is no guidance as to providing a synthetic material with radiopacity equivalent to bone.

Accordingly, there is a need in the art for a synthetic spinal implant material that does not carry the risk of disease transmission as with allograft materials.

There is also a need for a synthetic spinal implant material with a radiopacity similar to bone. A radiopacity similar to bone would allow for visualization of the implant between the vertebrae to assess radiographic fusion without distortion.

Further, there is a need for implants with mechanical properties similar to that of bone that can share the physiologic, dynamic compressive loads rather than shield them.

Moreover, there is a need for implants that are comprised of a material that bonds directly to bone and is bioactive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1A:
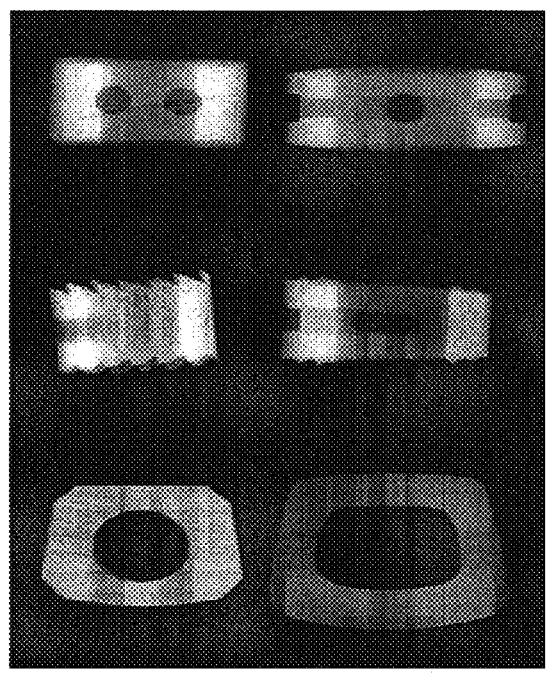
FIG. 1a provides a radiograph of implants of the present invention in comparison to allograft bone.

The present invention provides synthetic spinal implant materials that have a radiopacity similar to bone for facilitating radiographic assessment of fusion. The implant materials of the present invention are capable of withstanding physiologic dynamic, compressive loads and is bioactive and biocompatible. As defined herein, bioactive relates to the chemical formation of a calcium phosphate layer via ion exchange between surrounding fluid and the implant materials. Bioactive can also relate to materials that elicits a reaction which leads to bone formation or attachment into or adjacent to implants or to bone formation or apposition directly to the implants usually without intervening fibrous tissue. Biocompatible as defined herein relates to materials that do not invoke a prolonged adverse immunologic or host response. The present invention also provides methods for making such implant materials.

In certain embodiments of the present invention, the implant materials of the present invention can be comprised of a biocompatible polymeric matrix reinforced or coated with bioactive fillers and fibers. The implants can probably be comprised of a diurethane dimethacrylate (DUDMA) and tri-ethylene glycol dimethacrylate (TEGDMA) blended resin and a plurality of fillers and fibers including bioactive fillers and E-glass fibers. The implants may also be comprised of a variety of other monomers and fillers as described herein.

This invention teaches synthetic, bioactive spinal implant materials having a range of radiopacity from about 30 to about 55 and a range of stiffness from about 6 GPa to about 20 GPa. The invention also provides a synthetic, artificial shaped bodies in the form of a spinal implant, said implant shaped body having a radiopacity of about 30 to about 55 and a range of stiffness of about 6 GPa to about 20 GPa. Another embodiment discloses synthetic spinal implant materials that are optimized for radiopacity, stiffness, and bioactivity, comprising: a polymerizable resin matrix of DUDMA and TEGDMA resins and at least one filler.

The implant materials can be formed from a polymerized resin matrix and can include at least one filler that can be bioactive. A bioactive filler can comprise combeite. The polymerized matrix can comprise about 20% to about 50% of the total composition of the implant material. Fifty to about 80% of the filler can comprise the total composition of the implant material. The radiopacity of the implants can range from about 38 to about 50. Also, the stiffness can range from about 8 GPa to about 17 GPa.

Also included are methods of making a synthetic spinal implant material that is optimized for radiopacity, stiffness and bioactivity comprising: mixing a resin blend of DUDMA and TEGDMA mixing said resin blend with at least one filler, and agitating the to form said implant material.

The embodiment of this invention can be used to form a variety of different orthopaedic implants, particularly spinal implants having various shapes and sizes.

The present invention provides bioactive and biocompatible implant materials for formulation of shaped bodies capable of withstanding large dynamic, compressive loads, especially spinal implants. Further, the implant materials of the present invention overcome the risks associated with disease transmission present with allograft devices. Moreover, the implant materials of the present invention exhibit a radiopacity similar to that of bone.

The materials of this invention are preferably comprised of a biocompatible, hardenable polymeric matrix reinforced with bioactive and non-bioactive fillers. The materials can be comprised of about 10% to about 90% by weight of the polymeric matrix and about 10% to about 90% by weight of one or more fillers. The materials can also be comprised of about 20% to about 50% by weight of the polymeric matrix and about 50% to about 80% by weight of one or more fillers. In order to promote bone bonding to the implants, the implants of the present invention can be comprised of a bioactive material that can comprise a polymeric blended resin reinforced with bioactive ceramic fillers. Examples of such bioactive materials can be found, for example, in U.S. Pat. Nos. 5,681,872 and 5,914,356 and pending application U.S. Ser. No. 60/305,070, which is assigned to the assignee of the present invention and incorporated herein by reference in its entirety.

The polymeric matrixes of the implant materials are comprised of polymerizable monomer, monomers, dimers or trimers. They can comprise ethylenically unsaturated monomers or even an acrylate functional group. The term "monomers," as used herein, can also represent dimers, trimers, resins, resin components or any other polymerizable component. Examples of the monomers include, but are not limited to, DUDMA, bisphenol-A-glycidyl methacrylate (bis GMA), TEGDMA, ethoxylated bisphenol-A-dimethacrylate (bis-EMA), or combinations thereof. Still, further examples of monomers that can be used in the present invention include the adducts of 2,2,3-trimethylhexane diisocyanate with hydroxyethyl methacrylate, hydroxypropyl methacrylate, and other hydroxyacrylic acrylic species can also be used. Other examples of polymerizable species that can be used in the present invention include those disclosed in U.S. Pat. Nos. 5,681,872 and 5,914,356, and pending application U.S. Ser. No. 60/305,070, which are incorporated herein by reference in their entirety.

Methyl methacrylate, ethyl methacrylate, propyl methacrylate, higher methacrylates, acrylates, ethacrylates, and similar species can be employed as all or part of the polymerizable materials of the implant materials of the present invention. It is also possible to employ other types of polymerizable material such as epoxide compounds, polyurethane-precursor species and a wide host of other materials. For example, other monomers useful in the production of hardenable compositions of this invention include methyl-, ethyl, isopropyl-, tert-butyloctyl-, dodecyl-, cyclohexyl-, chloromethyl-, tetrachloroethyl-, perfluorooctyl-, hydroxyethyl-, hydroxypropyl-, hydroxybutyl-, 3-hydroxyphenyl-, 4-hydroxphenyl-, aminoethyl-, aminophenyl-, thiophenyl-, acrylate, methacrylate, ethacrylate, propacrylate, butacrylate, and chloromethacrylate, as well as the homologous monoacrylic acid esters of bisphenol-A, dihydroxydiphenyl sulfone, dihydroxydiphenyl ether, dihydroxybiphenyl, dihydroxydiphenyl sulfoxide, and 2,2 bis(4-hydroxy-2,3,5,6-tetrafluorophenyl)propane. Polymerizable monomers capable of sustaining a polymerization reaction such as the di-, tri-, and higher acrylic ethylene glycol dimethacrylate, diethylene glycol dimethacrylate, trimethylene glycol dimethacrylate, trimethylol propane trimethacrylate, analogous acrylates and similar species are also useful. It is also possible to employ mixtures of more than two polymerizable species to good effect.

The implant materials of the present invention can further comprise polymeric additives that include, but are not limited to, polymerization inhibitors, polymerization activators, polymerization initiators, stabilizers such as UV-9, radiopacifiers, reinforcing components (i.e., fibers, particles, micro spheres, flakes, etc.), bioactive fillers, neutralizing resins, diluting resins, antibiotic agents, coloring agents, plasticizers, coupling agents, free radical generators, radiographic contrast agents, and antibiotics.

In many embodiments, the implant materials include a monomeric blended resin of DUDMA to impart strength, TEDGMA to impart flexibility, a benzoyl peroxide initiator (BPO) or any peroxide initiator that is consumed during the polymerization reaction, and at least one polymer stabilizer. The implant materials can also include a plurality of fillers and fibers. The fillers can be of the combeite type, such as the combeite filler described in U.S. Pat. No. 5,681,872 to render the material bioactive and encourage direct bone bonding. Alternatively, the filler can be selected from a group of fillers including, but not limited to, borosilicate, silica, Wollastonite, hydroxyapatite (HA), beta-tricalcium phosphate, calcium sulfate, alumina, and the like. In embodiments where the implants further comprise fibers, the fibers can further include E-glass fibers of the composition type [$SiO_2$ CaO $Al_2O_3$ $B_2O_3$, A-glass fibers, silica or a plurality of other fibers including but not limited to Kevlar and carbon fibers for imparting toughness and strength to the implant. In certain embodiments, the fillers and fibers are surface treated for incorporation and bonding between them and the resin. For example, the fillers and fibers can be silanated, silicone-oil treated, or provided with coupling agents such alumina, titania, or zirconia coupling agents.

Certain embodiments have optimized radiopacity and stiffness and display bioactivity. As defined herein and in ASTM standards, radiopacity is calculated as an optical density ratio of the material versus an aluminum standard of the same thickness, both of which are normalized by the background sample optical density. The resultant number is multiplied by 100 and then referred to as the percent relative linear attenuation coefficient, $\alpha$, which is dimensionless. Embodiments of the present invention are synthetic, bioactive spinal implant materials having a radiopacity between about 30 to about 55 and stiffness between about 6 GPa to about 20 GPa. Other embodiments provide a synthetic, artificial shaped body in the form of a spinal implant, said shaped body having a radiopacity of about 30 to about 55 and a stiffness of about 6 GPa to about 20 GPa.

The radiopacity of bone ranges between about 24 to about 52 as reported by Brantigan, et al., "Compression Strength of Donor Bone for Posterior Interbody Fusion," *Spine*, 18, 1213–1221 (1983), with a stiffness ranging from about 3 GPa to about 17 GPa. Similar to bone, which is naturally bioactive, the present inventions also display bioactivity.

In other embodiments, the spinal implant materials can have a radiopacity of about 30 to 55 and a range of stiffness of about 8 GPa to 17 GPa. The spinal implant can be formed from a polymerized resin matrix. At least one filler can be included in other embodiments and any of the fillers can be bioactive. The bioactive filler can be combeite glass ceramic or another type of ceramic filler. In some embodiments, the polymerized resin matrix comprises about 20% to about 50% of the total composition of the implant material. About 50% to about 80% of the total composition of the implant material can be filler.

Certain embodiments are synthetic spinal implant materials that are optimized for radiopacity, stiffness, and bioactivity, comprising a polymerizable resin matrix of DUDMA and TEGDMA resins and at least one filler.

While the present invention material has been described in terms of polymeric matrices comprised of polymerizable monomers and the like, it should be understood that the disclosed radiopacity and stiffness ranges may be achieved by using a variety of materials. For instance, the polymeric matrix may be composed of any polymeric material and include an additional organic or inorganic component. The matrix may be thermoplastic, thermoset, polymerizable, or non-polymerizable. Epoxies, polyurethanes, polyphosphates, polyesters, polyamides, polyphosphazenes, polycarbonates, polyureas, polyamides, polyacrylonitriles, polysulfones, polysulfides, polysiloxanes, polyacetals, polyethers such as polyetheretherketone (PEEK), fluoropolymers, polyketals, polyolefins such as polyethylene (PE), polypropylene (PP), polystyrene, and polyvinylchloride (PVC), and the like may also be used. These materials may be used either alone, in combination, or with various fillers to form a copolymer or terpolymer with the present invention to provide an implant material that yields desired radiopacity and stiffness comparable to bone as described herein.

Also included as a part of the present invention are methods of making a synthetic implant material that is optimized for radiopacity, stiffness, and bioactivity, comprising mixing a resin blend of DUDMA, TEGDMA, and a stabilizer, mixing said resin blend with at least one filler, and agitating the resultant mixture to form said implant material. The resin blend can also comprise an initiator. Both mixing steps can occur under vacuum. The fillers can be added in the range of about 15% by weight to about 80% by weight of the total mixture composition. If vacuum is applied at this stage, it can be applied upon the addition of each filler. Agitation of the resultant mixture can be added to further eliminate bubbles or voids.

In one embodiment of the present invention, the monomers, fillers, and other additives are blended together to form a paste composition. The paste compositions are easily mixed via a low speed, high shear rotary mixer. The duration of the blending operation will vary depending upon the constituents that comprise the paste composition precursors. In one embodiment, the blending of the monomers and other additives within the paste composition precursors activates the polymerization of the composition. In another embodiment, exposure to heat either during or after blending activates the polymerization. The exposure can occur in temperature ranges of about 40° C. to about 180° C. or about 60° C. to about 120° C. in some instances.

The implant materials of the present invention can be comprised of a one paste system or combined with two or more paste compositions to form a multiple paste system. Depending upon whether the implant material is a one paste or multiple paste system determines the hardening of the material. The paste compositions of the present invention can be hardened under the influence of heat, photochemical energy, chemically, or in a controlled fashion. In certain embodiments wherein the implant materials comprise a one paste system, the paste composition is hardened or cured via exposure to heat or light. Alternatively, the paste composition could be cured via gamma radiation. In some embodiments, additional exposure to gamma radiation can impart additional strength. In other embodiments wherein the implant materials comprise a multiple paste system, the paste compositions are admixed and hardened via thermal energy or heat cured. The paste compositions can also be chemically cured via catalyst or redox systems. It will be understood, however, that a wide variety of polymerization systems and materials for use therein can be employed to good advantage in connection with the present invention and all such systems are contemplated hereby. Depending upon the system that is employed, the paste composition can generally comprise heat-curing catalysts, photopolymerization, or redox (i.e. N,N(dihydroxyethyl)-p-toluidine(DHEPT), BPO, FeII, tertiary butyl hydroperoxide (t-BHP)) initiators. Each type is well-known and any catalytic system known for restorative use can be employed so long as the same is consistent with the objects of the invention.

In multiple paste systems where heat curing is used to harden the composition, a catalytic system is employed such that when two components of the hardenable composition are mixed together, the catalytic action begins, leading to hardening. This system is familiar and can be applied to a wide variety of polymerizable species including many which are suitable in the present invention. Radical initiators such as peroxides, especially benzoyl peroxide (also called dibenzoyl peroxide) are conventional, economic and convenient. A stabilizer such as butyl hydroxy toluene is customary, as is employment of co-catalysts like dimethyl-p-toluidine, N-N-substituted toluidine, and other conventional catalysts including tertiary amine structures with double bond functionality like diethyl aminoethyl methacrylate and N,N-dimethyl-p-toluidine. In general, one of the pastes incorporates both the radical initiator and stabilizer, such as a peroxide, and the other paste incorporates the accelerator, such as an amine or toluidine. Curing is initiated by an oxidation-reduction mechanism upon mixing the two pastes together.

In paste systems where curing via exposure to heat or other means is used to harden the composition, a photoinitiation system can be included with the hardenable compositions and the same caused to be activated by exposure to actinic light of a suitable wavelength. Both ultraviolet and visible photocuring systems are known for use in restorative surgery and dentistry and any such system can be employed herein. Exemplary systems are described in U.S. Pat. No. 4,110,184 to Dart et al., U.S. Pat. No. 4,698,373 to Tateosian et al., U.S. Pat. No. 4,491,453 to Koblitz et al., and U.S. Pat. No. 4,801,528 to Bennett, which are incorporated herein by reference in their entirety to provide enablement for such, known systems.

A particularly useful system employs visible light curing, thus avoiding the potential danger inherent in curing with ultraviolet radiation. Visible light curing has been well refined in the dental field and the same can also be applied to restorations of bony tissues. Quinones, as a class, find wide utility as photochemical initiators for visible light sensitizing systems, preferably when the same are admixed with tertiary amines. Some skilled artisans may prefer that an alpha diketone (quinone) such as camphoroquinone or biacetyl be admixed with an amine reducing agent such as n-alkyl dialkanolamine or trialkanolamine. Other such photo-initiator systems include a 2-Benzyl-2-(dimethylamino)-4'-morpholinobutyrophenone, or 50%/50% weight composition of 2-Hydroxyethyl-2-methyl-1-phenyl-1-propanone and Diphenyl (2,4,6-trimethylbenzyl) phosphine oxide. However, other such curing systems or combinations of curing systems can also be employed with the materials of the present invention.

In some embodiments, the paste system is not cured or hardened but used in situations in which the paste form is preferred. In those cases, the paste may be dispensed from a tube or the like. In other embodiments, one or more fillers are blended into the paste composition after the monomers and other additives comprising the resin blend have been combined. The fillers can be added incrementally to avoid binding during the blending process. A vacuum can be applied during blending to minimize porosity and dusting. Some embodiments comprise multiple fillers, which may include E-glass fibers and fillers or fibers of borosilicate, silica, and combeite. In particular embodiments, the E-glass fibers can be added first followed by the remaining fillers in a designated order. Alternatively, one or more fillers can be pre-blended together prior to incorporation into the resin blend. After the filler has been combined with the resin mixture, the completed paste mixture can be agitated via a vibrating table, ultrasonic or similar means for a period of time ranging from about 5 minutes to about 60 minutes to further reduce porosity. A vacuum can be applied during the agitation step.

Table I shows a number of compositions in accordance with certain preferred embodiments of the present invention together with salient data showing suitability for orthopaedic, especially spine implant use. Six exemplary implant materials were made in accordance with the present invention. The weight percentage of each composition is presented in the table. As the following table illustrates, the Examples 2–4 are multiple paste systems wherein Examples 5–7 are one paste systems.

The implant materials of Examples 2–7 can be fashioned into standard shapes, which include cylinders, bricks, and dog bones, for testing. Along with radiopacity, the compressive strength, compressive yield, and compressive modulus were tested, as were the tensile strength and tensile modulus. Compressive testing was conducted in accordance with ASTM D 695-91 using 6 mm diameter×12 mm height cylindrical specimens. Tensile testing was conducted in accordance with ASTM D 638-95, using Type IV specimen geometry of flat tensile bars or "dog bone". Lastly, radiopacity was conducted in accordance with ASTM F 640-79 ("Radiopacity of Plastics for Medical Use").

TABLE I

|  | Comparison | | | | | |
| --- | --- | --- | --- | --- | --- | --- |
|  | Ex. 2 | Ex. 3 | Ex. 4 | Ex. 5 | Ex. 6 | Ex. 7 |
| Formulation Comparison [Product (%)] | | | | | | |
| Bis-GMA | 12–14 | 13–15 | 0–1 | 0–1 | 0–1 | 0–1 |
| Bis-EMA | 5–7 | 6–8 | 0–1 | 0–1 | 0–1 | 0–1 |
| TEGDMA | 11–13 | 12–14 | 8–10 | 7–9 | 7–9 | 7–9 |
| DUDMA | 0–1 | 0–1 | 24–28 | 24–28 | 24–28 | 24–28 |
| t-Butylhydroxytoluene | 0–1 | 0–1 | 0–1 | 0–1 | 0–1 | 0–1 |
| DHEPT | 0–1 | 0–1 | 0–1 | 0–1 | 0–1 | 0–1 |
| UV-9 ($C_{14}H_{12}O_3$) | 0–1 | 0–1 | 0–1 | 0–1 | 0–1 | 0–1 |
| BPO | 0–1 | 0–1 | 0–1 | 0–1 | 0–1 | 0–1 |
| Silane Treated Amorphous Silica | 7–9 | 6–8 | 6–8 | 4–6 | 4–6 | 4–6 |
| Silane Treated Orthovita Combeite [OC] Filler | 28–31 | 18–21 | 18–21 | 20–23 | 22–24 | 19–21 |
| Silane Treated Bariaboroaluminosilicate Glass | 29–32 | 0–1 | 0–1 | 0–1 | 0–1 | 0–1 |
| Silane Treated Alkali Leached OC Filler | 0–1 | 16–19 | 16–19 | 20–23 | 19–21 | 0–1 |
| Silane Treated E-Glass | 0–1 | 19–21 | 19–21 | 19–21 | 19–21 | 19–21 |
| Silane Treated Borosilicate Filler | 0–1 | 0–1 | 0–1 | 0–1 | 0–1 | 22–24 |
| Approx. Test Parameter before Gamma Irradiation | | | | | | |
| Compressive Strength (MPa) | 211 | — | — | 195.6 | 216.3 | 238.4 |
| Compressive Yield (MPa) | 127 | 105 | 125 | 150 | 170 | 182 |
| Compressive Modulus (MPa) | 5800 | 6998 | 7875 | 8456 | 8403 | 8516 |
| Tensile Strength (MPa) | 52.5 | 60.2 | 54.3 | — | 63.4 | 86.7 |
| Tensile Modulus (MPa) | 9800 | 10306 | 11976 | — | 14839 | 16290 |
| Radiopacity | 118.6 | — | 50 | — | 46.3 | 57.3 |

Although the uses described above are exemplary for the present invention, there are other embodiments that may be foreseen by those skilled in the art. Within the dental field, the implants of the present invention can have use as dental crowns (temporary or crown) and dental implants, including Maryland bridges. The implant materials can also have use as implants for other areas of the animal body. Such foreseeable implants include cochlear, cranial, tumor, sternum, or other custom implants that can be MRI compatible or functional shapes made for the body. Other embodiments can be used for formulation of universal plates for orthopedic use, bone screws, rods, and pins for orthopedic use (IM nails, femoral rods or plugs, long bone fractures, etc.), tendon anchors, suture anchors and tacks, graft retainers, and marrow sampling ports.

Other pharmaceutical uses include non-articulating artificial joint surfaces, sensor anchors or housings, bone spacers or wedges (tibial, femoral), cartilage beds or anchors, or drug delivery. It is also foreseeable that the implant materials can be used in methods for repairing the iliac harvest site. The materials can be incorporated into drug delivery beads into bone or in interbody balls. There can also be applications for mandibular joints (TMJ) and orbital reconstruction.

One embodiment of the present invention involves machining of the implantable materials into morsels for use in methods to treat segmental defects. The morsels can also be used for minimally invasive load bearing applications. The material can be made into a mesh for postero-lateral fusion or cages for other materials. Other embodiments involve the material being used as a cannulated screw with peripheral holes used in methods for treating vertebral augmentation. The present invention can have embodiments involving synthetic bones.

EXAMPLES

Example 1

Bioactive Spinal Implant Material

An exemplary implant material for the manufacture of spinal implants in accordance with the invention was formulated to exhibit biocompatibility and bioactivity for bone bonding, radiopacity similar to bone in order to be able to assess fusion, mechanical strength to support physiologic loads, and bone-like stiffness to allow for good load sharing among the elements of the spine.

One implant material includes a polymeric blended resin, comprising 20% to about 50% by weight of the implant material total composition. The resin blend can be further comprised of from about 30% to about 90% by weight of resin DUDMA, about 10% to about 60% by weight of resin TEGDMA, about 0.1% to about 4% by weight of BPO, and 0% to about 0.25% by weight of butylated hydroxy toluene (BHT).

The remainder of the implant material is comprised of a plurality of fillers. The fillers can be further comprised of from about 0% to about 40% by weight of filler surface treated E-glass® fibers to impart fracture toughness and mechanical strength and having have an average length of about 3000 μm or less and an average diameter range of about 5 μm to 50 μm; about 5% to about 50% by weight of filler surface treated, silanated combeite filler having bioactive characteristics which promote bone bonding; about 0% to about 50% by weight of filler of a surface treated borosilicate glass filler having an average diameter of –10 μm (e.g., 90% of the particles have a diameter of less than 10 μm, measured by laser analysis); and about 0% to about 30% by weight of filler of a surface treated silica for imparting mechanical strength and to act as a rheology modifier. In this particular example, the filler is comprised of about 20% by weight surface treated E-glass® fibers, about 20% by weight of filler surface treated, silanated combeite filler, about 23% by weight of filler of a surface treated borosilicate glass filler, and about 5% by weight of filler is surface treated silica. Once all components are combined, the formulated material is hardened via conventional heating processes, which initiates the polymerization reaction.

Example 2

Radiopacity of a Bioactive Spinal Implant Material

Figure 1B:
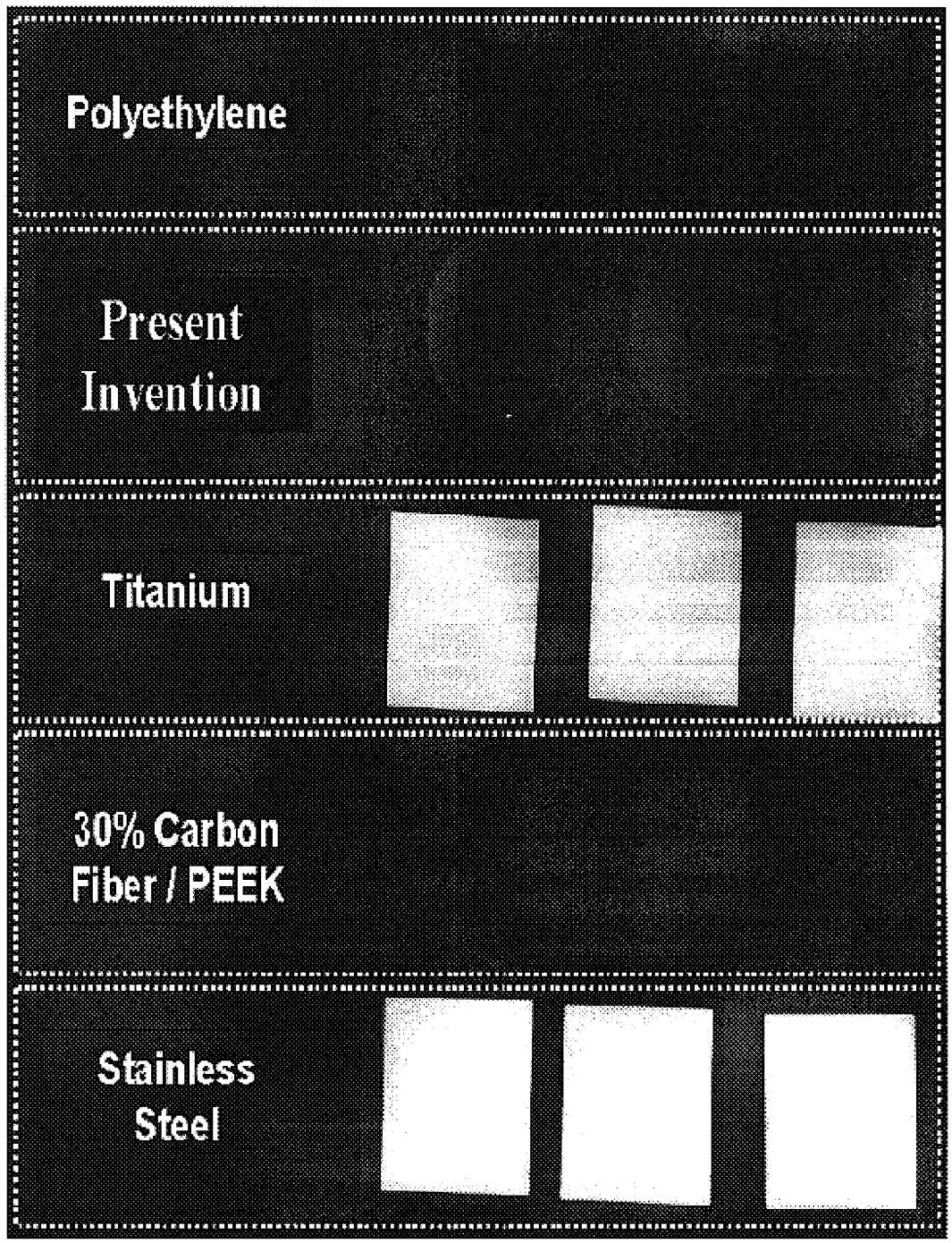
FIGS. 1b and 1c provide a radiograph of the present invention material in comparison to other standard materials.
Figure 1C:
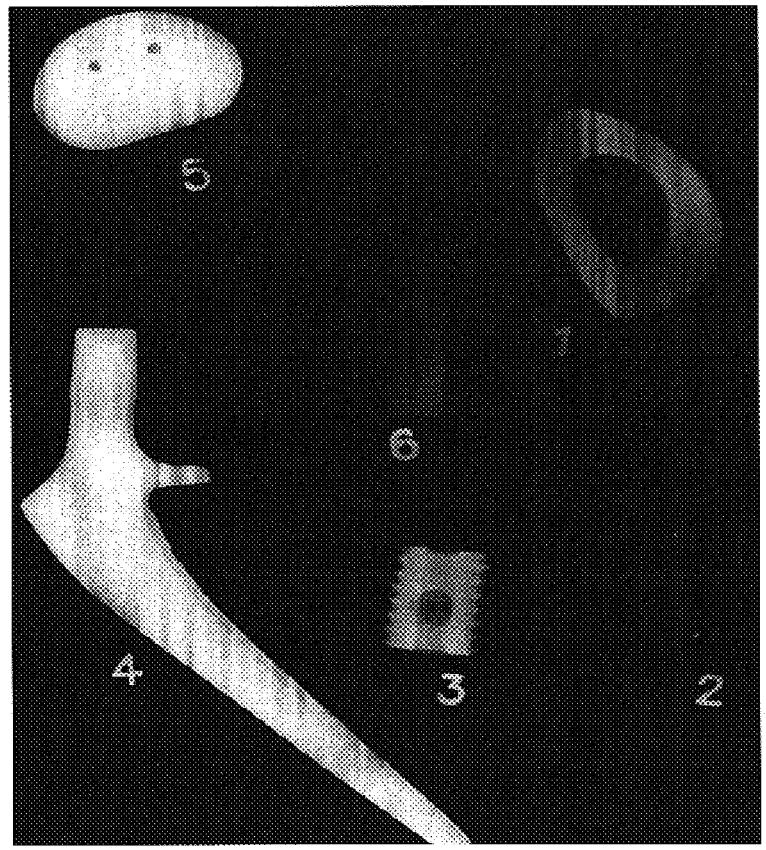

Qualitative Evaluation: Material of the present invention was prepared in the shape of an implant, which was placed along side an allograft implant for qualitative radiographic assessment as shown in FIG. 1a. Visually the samples had a similar radiographic appearance. In comparison to standard materials (FIG. 1b), the radiographic appearance of the material of the present invention most closely resembles bone. Variations of the present invention material can be formulated to produce variations in radiopacity as shown in FIG. 1c.

B) Quantitative Evaluation: Three tensile bar samples of polymerized bioactive material of the type described herein, approximately 4 mm in thickness, were arranged onto x-ray film, and a 16-step Aluminum step was placed on top. The 10-mm thick Aluminum step was placed so that it was partly shielding a polymerized sample and partly over x-ray film only (these materials were situated in a Faxitron x-ray cabinet). The use of an Aluminum background allowed for more reproducible comparison between x-rays than the use of exposed film alone. The other two samples were placed at the ends of the wedge in order to balance it.

The lowest stage in the Faxitron cabinet was used and its focus-film distance was 50 mm. The 4-mm thick samples were exposed using appropriate exposure time and voltage (180 sec., 80 kVp). A background optical density ranging from 0.8 to 1.2 defined an appropriate exposure.

After the film had been exposed to x-rays, it was removed from the Faxitron and developed.

Using the densitometer, Background (B), Sample (S) and Aluminum (A) density values were recorded.

The same process was used to determine the radiopacity values of gamma irradiated material as prepared in accordance with Example 1 above.

Calculations

The percent relative linear attenuation coefficient, α, was calculated as follows:

$$\alpha = \frac{(B-S)}{(B-A)} \times 100$$

where:
B=background optical density of 10 mm of Al, in the range of 0.8 to 1.2.
A=optical density under the 14 mm thickness of Al (4 mm Al sample added to 10 mm Al background), and
S=optical density of the image of the 4 mm thick sample.

Results

Quantitatively, the material, before gamma irradiation, had an average radiopacity value of 45.55.

TABLE II

Optical density values for three lots of material prior to gamma irradiation.

| Lot Number | Sample | Back-ground, B | Sample, S | Aluminum, A | Linear attenuation coefficient, α |
|---|---|---|---|---|---|
| 022601-067 | 1 | 0.89 | 0.76 | 0.58 | 41.94 |
|  | 2 | 0.86 | 0.73 | 0.57 | 44.83 |
|  | 3 | 0.92 | 0.78 | 0.61 | 45.16 |
|  | Mean | 0.89 | 0.76 | 0.59 | 43.98 |
|  | S.D. | 0.03 | 0.03 | 0.02 | 1.77 |
| 022601-074 | 1 | 0.92 | 0.78 | 0.61 | 45.16 |
|  | 2 | 0.83 | 0.71 | 0.55 | 42.86 |
|  | 3 | 0.93 | 0.78 | 0.60 | 45.45 |
|  | Mean | 0.89 | 0.76 | 0.59 | 44.49 |
|  | S.D. | 0.06 | 0.04 | 0.03 | 1.42 |
| 032601-082 | 1 | 0.92 | 0.78 | 0.60 | 43.75 |
|  | 2 | 0.91 | 0.77 | 0.66 | 56.00 |
|  | 3 | 0.85 | 0.72 | 0.56 | 44.83 |
|  | Mean | 0.89 | 0.76 | 0.61 | 48.19 |
|  | S.D. | 0.04 | 0.03 | 0.05 | 6.78 |
| 022601-067 | Mean | 0.89 | 0.76 | 0.59 | 43.98 |
| 022601-074 | Mean | 0.89 | 0.76 | 0.59 | 44.49 |
| 032601-082 | Mean | 0.89 | 0.76 | 0.61 | 48.19 |
|  | Mean | 0.89 | 0.76 | 0.60 | 45.55 |
|  | S.D. | 0.00 | 0.00 | 0.01 | 2.30 |

Quantitatively, the material, after gamma irradiation, had an average radiopacity value of 42.94.

TABLE III

Optical density values for three lots of material after gamma irradiation

| Lot Number | Sample | Back-ground, B | Sample, S | Aluminum, A | Linear attenuation coefficient, α |
|---|---|---|---|---|---|
| 022601-067 | 1 | 1.01 | 0.85 | 0.62 | 41.03 |
|  | 2 | 0.99 | 0.84 | 0.63 | 41.67 |
|  | 3 | 1.05 | 0.89 | 0.68 | 43.24 |
|  | Mean | 1.02 | 0.86 | 0.64 | 41.98 |
|  | S.D. | 0.03 | 0.03 | 0.03 | 1.14 |
| 022601-074 | 1 | 1.01 | 0.85 | 0.64 | 43.24 |
|  | 2 | 1.00 | 0.84 | 0.62 | 42.11 |
|  | 3 | 1.01 | 0.85 | 0.64 | 43.24 |
|  | Mean | 1.01 | 0.85 | 0.63 | 42.86 |
|  | S.D. | 0.01 | 0.01 | 0.01 | 0.66 |
| 032601-082 | 1 | 0.99 | 0.84 | 0.63 | 41.67 |
|  | 2 | 0.98 | 0.83 | 0.62 | 41.67 |
|  | 3 | 1.01 | 0.83 | 0.64 | 48.65 |
|  | Mean | 0.99 | 0.83 | 0.63 | 43.99 |
|  | S.D. | 0.02 | 0.01 | 0.01 | 4.03 |
| 022601-067 | Mean | 1.02 | 0.86 | 0.64 | 41.98 |
| 022601-074 | Mean | 1.01 | 0.85 | 0.63 | 42.86 |
| 032601-082 | Mean | 0.99 | 0.83 | 0.63 | 43.99 |
|  | Mean | 1.01 | 0.85 | 0.63 | 42.94 |
|  | S.D. | 0.02 | 0.02 | 0.01 | 1.01 |

Conclusions

A total of three lots of polymerized bioactive material consisting of three samples per lot of material was evaluated and compared directly to Aluminum for radiopacity determination. All testing was conducted in accordance with Orthovita's Technical Operating Procedure. Results summarized in the preceding tables indicate that the bioactive spinal material has an average radiopacity value of 45.55 before gamma irradiation and a radiopacity value of 42.94 after gamma irradiation. Statistical analysis of results demonstrates that there is not a significant amount of variance between lots and data records, p=0.445 for pre-gamma data and p=0.624 for post-gamma data. Statistical analysis also shows that there is not a significant amount of variance between pre and post gamma data. This indicates that gamma irradiation does not significantly affect the radiopacity of the material.

Radiopacity of polymerized material for medical use is clinically important due to the frequency of using x-rays in measuring the placement, function, form, and effectiveness of the material. Both pre and post gamma bioactive implants have a radiopacity value that will allow for good radiographic viewing that will aid in the placement and postoperative monitoring of spinal implants made from this material. Radiopacity values for the bioactive spinal implant material of the present invention compare favorably with human bone, which has a radiopacity range of about between 24 to 52.

Figure 2A:
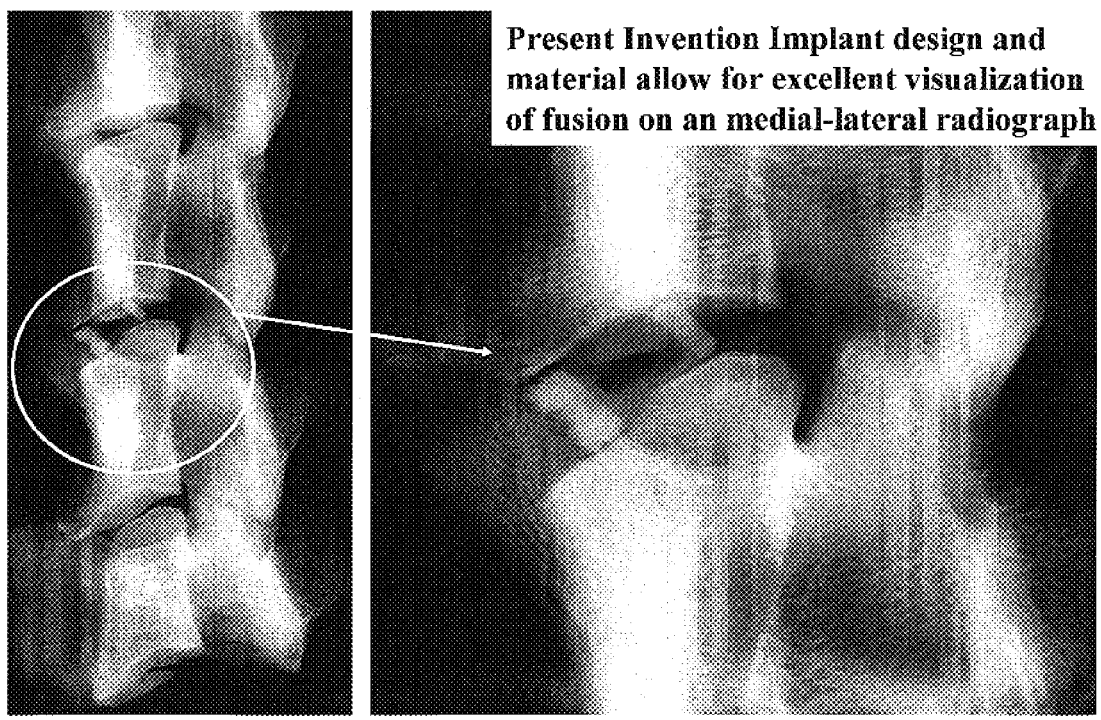
FIG. 2a provides a radiograph of an implant of the present invention after insertion between adjacent vertebrae in a sheep spine, and FIGS. 2b and 2c provide a radiograph and corresponding image, respectively, of a present invention implant (top) in comparison to a titanium implant (bottom) in a calf spine.

As observed in FIG. 2a, the radiopacity of the material of the present invention allows for visualization of the implant between adjacent vertebral bodies (in this case in a segment of a sheep spine), as well as visualization for the eventual assessment of fusion from a medial-lateral radiograph. This observation is also noted in FIGS. 2b and 2c in comparison to a titanium implant.

Example 3

Mechanical Properties of a Bioactive Spinal Implant Material

Samples were prepared using the bioactive material described herein. Tests were performed using ASTM Guidelines on an Instron Model 8516 in order to obtain ranges of values of mechanical properties of the material as shown in the table below.

TABLE IV

Mechanical Properties of a Bioactive Spinal Implant Material

| TEST | RESULT | HUMAN CORTICAL BONE LITERATURE |
|---|---|---|
| Compressive Strength ASTM F 451-95 & ASTM D695-91 | 220–250 MPa | 167–215 MPa |
| Compressive Modulus ASTM F 451-95 & ASTM D695-91 | 7.0–9.0 GPa | 14.7–19.7 MPa |
| Compressive Yield Strength ASTM F 451-95 & ASTM D695-91 | 170–182 MPa | 121–182 MPa |
| Tensile Strength ASTM D638-98 | 65–100 MPa | 70–140 MPa |
| Tensile Elastic Modulus ASTM D638-98 | 14–17 GPa | 10.9–14.8 MPa |
| 3-Point Flexural Strength ASTM D790-90 | 100–120 MPa | 103–238 MPa |
| Shear by Punch Tool ASTM D732-93 | 60–80 MPa | 51.6 MPa |
| Compressive Fatigue Strength ($10^6$ cycles) | 170–190 MPa | >100 MPa |
| Tensile Fatigue Strength ($10^6$ cycles) | 35–55 MPa | 49 MPa |

Example 4

Bioactivity Testing of a Spinal Implant

Bioactivity testing was performed on disc shaped implants comprised of the material described herein. Bioactivity as used throughout this disclosure is defined as the ability of the implant to form a calcium phosphate layer on its surface.

Uncured samples of the material described in Example 1 were injected into 5 cc syringes. The material was heated at 100° C. for 1 hour for complete polymerization. The rods formed within the syringe were cut into thin disks (approximately 1 mm thick) using a Buehler diamond blade saw. Simulated body fluid (SBF) was prepared according to the Kokubo recipe (fluid which simulates blood plasma) and using a balance, 250 grams of simulated body fluid was weighed into 5 high density polyethylene (HDPE) bottles. One disk of material was placed in each of the five bottles. The containers of SBF containing the disks were placed at 37° C. for specified intervals. The time intervals were 6, 12, 19, 30 and 50 days. A sample size of 1 disk was prepared at each time period. At these time points, one disk of material was removed from its bottle. The sample was dried with compressed air prior to analysis. The SBF was not analyzed prior to immersion of samples and was discarded after the last sample was removed.

As a non-destructive test, Fourier Transform Infrared Spectroscopy (FTIR) was performed first on the samples. The samples were analyzed using the Nicolet Instruments Magna 560 FTIR. The stage used for this analysis was a single-bounce Attenuated Total Reflectance (ATR) with a diamond crystal and KRS-5 lenses. This stage permitted a surface analysis of the composites through the entire mid-infrared spectrum from 4000 to 400 cm-1. The samples were analyzed at a 4 cm-1 resolution. The samples were placed in direct contact with the ATR crystal. Contact was maximized via an anvil on the opposite side of the sample. Spectra were collected on several areas of the composite samples. At each time point, spectra were analyzed for the presence of key calcium phosphate bands as compared to the Day 0 control.

After FTIR analysis, the same samples were then used for Scanning Electron Microscopy/Energy Dispersive Spectroscopy (SEM/EDS). Samples were coated with a thin layer of gold-palladium using a Hummer Sputter Coater. Samples were painted with a small amount of conductive silver paint, when necessary. The operation procedure of the SEM analysis followed the standard procedure for the operation of the JEOL JSM-840A and the EDS analysis. A few of the thin disks were cut exposing the cross-section of the composite. The cross-sections were embedded in epoxy resin revealing the cut surface. Upon complete curing of the epoxy, samples were polished on the Buehler EcoMet3. Final polishing consisted of a 1-micron diamond suspension.

The characterization of bioactivity of the polymerized composite surface by scanning electron microscopy consisted of the following parameters: appearance of calcium phosphate deposition (white in back-scattered electron imaging "BSEI" mode) and thickness of calcium phosphate layer. The characterization of bioactivity of the polymerized composite surface by energy dispersive spectroscopy consisted of the following parameters: calcium and phosphorous detection and reduction in sodium levels at a bioactive filler.

FTIR Results

Figure 3:
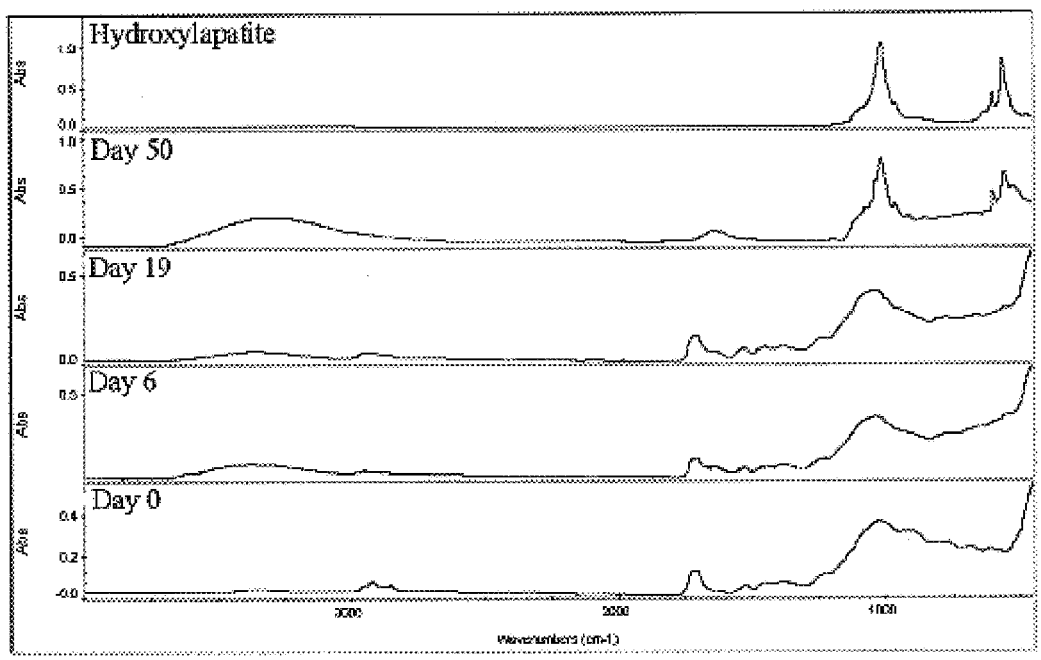
FIG. 3 provides Fourier Transform Infrared Spectroscopy (FTIR) spectrum of the material of the present invention from an in vitro bioactivity test at Day 0, 6, 19 and 50 in comparison to hydroxylapatite.

The Rhakoss FTIR results are shown in FIG. 3. The displayed results show few spectral changes are observed in the early time periods. However, the Day 50 spectrum demonstrates dramatic changes and is very similar to hydroxyapatite. The Day 50 results show the maturity of the calcium phosphate growing on the material. Note the sharpness of the 1014 cm-1 band in Day 50 spectra.

The following table outlines the peaks seen on the material in comparison with hydroxyapatite at Day 50 and the molecular assignments:

TABLE V

FTIR Peaks of the Material of the
Present Invention and Hydroxyapatite

| ABSORBANCE BAND (cm$^{-1}$) | | |
|---|---|---|
| HYDROXYAPATITE | RHAKOSS | MOLECULAR ASSIGNMENT |
| — | 3292 | O—H and hydrogen bonding from residual water on the composite |
| — | 1632 | Olefin stretch from the composite |
| 1092 | 1075 | Three components of the out of phase stretch of the phosphate ion |
| 1014 | 1014 | |
| 956 | 960 | |
| — | — | Possibly an out of phase deformation band of a carbonate ion resulting from residual SBF salt |
| 602 | 598 | A split bending mode of the phosphate ion |
| 559 | 556 | |

SEM/EDS Results

Figure 4:
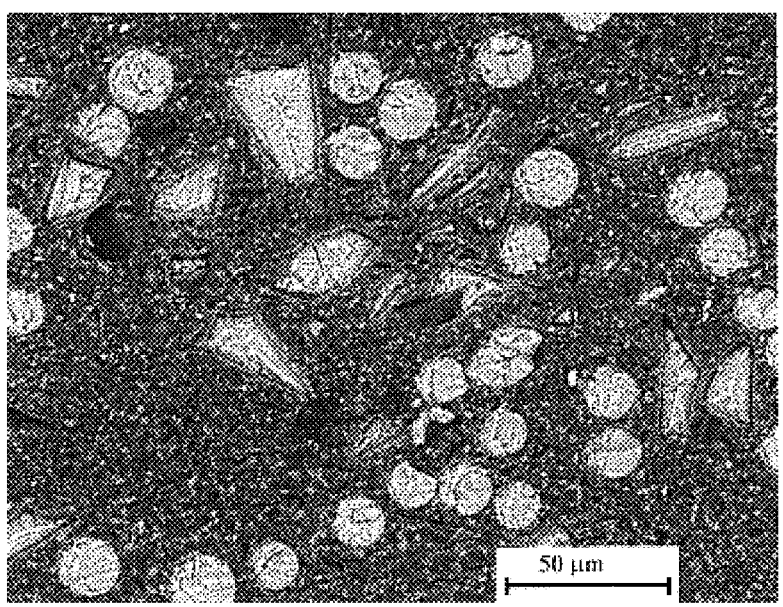
FIG. 4 provides back-scattered electron (BSE) microscopy images of the material of the present invention at Day 0.
Figure 5:
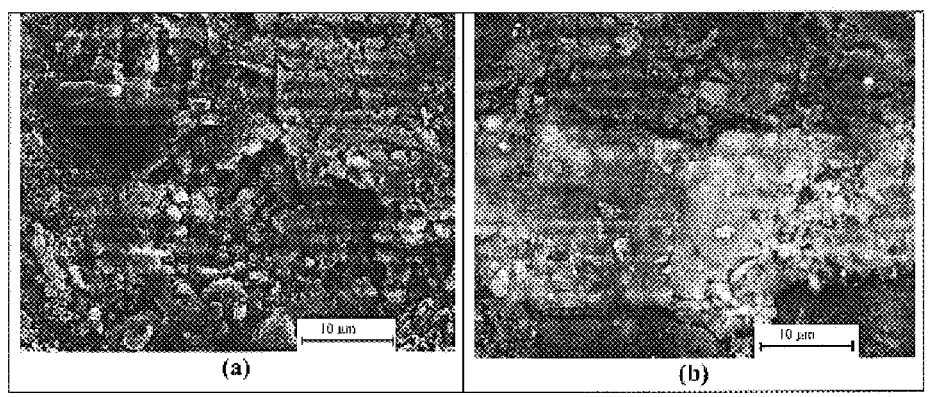
FIG. 5 provides (a) a Scanning Electron Microscopy (SEM) image of a Day 6 sample of the material of the present invention from an in vitro bioactivity test with a layer of calcium phosphate on the surface of a bioactive filler (2500×), (b) SEM of a cross-section of Day 19 with a CaP growth on the surface of a bioactive filler (2500×).

Day 0 back-scattered electron (BSE) image of a cross-section of the material is illustrated in FIG. 4 (500×). The material demonstrated a calcium phosphate crystal (CaP) as early as 6 days as confirmed by EDS analysis. The Day 6 sample showed the growth was limited to a few bioactive fillers. The Day 19 sample showed little differences from the earlier time period as demonstrated in FIG. 5.

Figure 6:
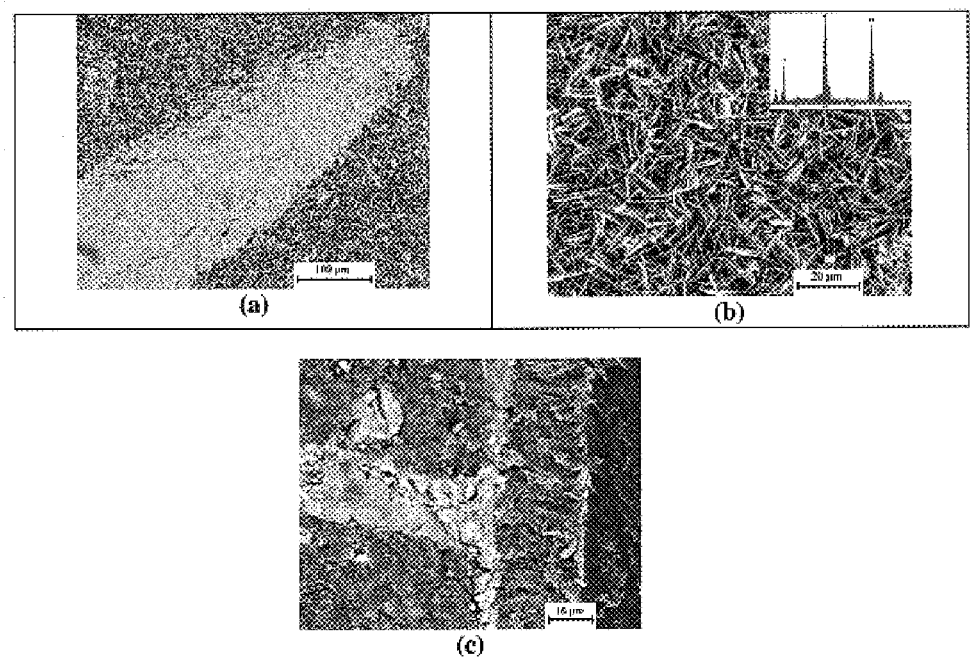
FIG. 6 provides (a) SEM of a Day 50 sample of the material of the present invention with a layer of CaP on its surface (250×), (b) SEM of a Day 50 sample of the material of the present invention with a thick, dense, needlelike growth of CaP on it surface (1000×) (c) SEM of a cross-section of a Day 50 sample of the material of the present invention, CaP has covered the surface and grown into the bioactive filler (1500×).

By 50 days, the material exhibited a thick, dense CaP layer. Again, this layer covered the entire surface of the composite. The CaP crystals were mature with the appearance of stacked plates. The CaP thickness was measured as approximately 10 microns, and was interdigitated into bioactive fillers at the surface of the composite. FIG. 6 illustrates the CaP crystal on the surface of Rhakoss.

FTIR Conclusions

The early FTIR results showed few spectral changes in the material. Both the Day 6 and Day 19 samples showed the same type of strong organic absorptions as seen in the Day 0 sample.

By Day 50, the material exhibited a thick surface coating of calcium phosphate. Spectra taken at various locations on the material showed only inorganic phosphate absorbencies, and none of the organic bands seen in the previous samples (Day 0, 6, and 19). The depth of penetration for this FTIR technique is 2-microns. This indicates that the thickness of the calcium phosphate growth is at least 2-microns thick.

The Day 50 spectra were compared against several types of calcium phosphates in the User library. The best spectral match for both samples was hydroxyapatite. This close match indicates that hydroxyapatite is the calcium phosphate species growing on the sample surface. The primary hydroxyapatite band seen occurs around 1014 cm-1. This band demonstrates a more resolved hydroxyapatite shoulder at 955 cm-1, pointing to a mature species.

SEM/EDS Conclusions

At the Day 50 time period, the material appears to have a larger surface coverage of calcium phosphate and a thickness of CaP deposition. The evaluations of the cross-sectioned samples provided an accurate measurement of the CaP thickness. Also, he CaP layer was evaluated for its interdigitation into the composite. Several observations of the CaP migrating into a bioactive E-glass ceramic filler at the surface were noted.

Based on the results presented herein, the material of the present invention can be described as bioactive.

Example 5

Static Compression and Compression Shear of a Cervical Implant

Static compression was performed on 6 spinal implants with a 7° lordotic angle. All implants withstood at least 8.1 kN of axial load before yielding. In compression-shear testing, the weakest implant type (6 mm extra wide) had a yield of approximately 2.7 kN. Note that human cervical endplates fail at 2.0 kN direct compression.

Example 6

Fatigue Test (Compression) of Cervical Implant

Fatigue testing was performed on 6 spinal implants. All implants successfully withstood 5×10$^6$ cycles in 37° C. phosphate buffered saline solution at a 5 Hz loading frequency from −50 N to −500 N with negligible deformation.

Example 7

Compression Tests of Spinal Implant

A) An axial compression test was performed on one embodiment of a spinal implant using an Instron 8516 at a crosshead speed of 1.5 mm/min. Glassfilled Delrin was used as an interface between the implant and the steel fixtures. The Delrin was machined to mate approximately with the angle of the implant design. The implant was designed to include a 5° lordotic angle.

Implant failure occurred at approximately 41 kN (about 9000 lbf), approximately 12 times body weight.

B) An axial compression test was performed on two spinal ALIF implants and one cervical spinal implant using an Instron 8516 at a crosshead speed of 1.5 mm/min. Polyacetal inserts were machined to match each of the implant's lordotic angle and/or superior and inferior surface contours (e.g., convex top and bottom surfaces). The two ALIF implants had a maximum implant height of 10 mm and a 5° lordotic angle. Failure occurred at loads of 31 kN and 48.8 kN (10,960 lbf), respectively. The cervical implant had a maximum implant height of 10 mm and 7° lordotic angle. Failure occurred at a load of 14.1 kN (3170 lbf).

Example 8

Biocompatibility of a Spinal Implant

Samples of a bioactive spinal implant material were tested for biocompatibility using ISO Guidelines 10993-1, *Biological evaluation of medical devices*. Under these guidelines and in compliance with U.S. Food and Drug Administration's Good Laboratory Practice Regulation, 21 CFR, Part 58, the material was evaluated for cytotoxicity, sensitization, intracutaneous reactivity, acute toxicity, and genotoxicity. All results were negative and showed the material to be non-cytotoxic, non-allergenic, a non-irritant, non-toxic, non-mutagenic, and non-genotoxic. In addition, material exhibits a degree of polymerization above 98% and analysis revealed organic leachate less than 0.01 ppm/g of monomer elution.

Example 9

In Vivo Implantation of a Spinal Implant

Spinal implants were implanted in three non-human primates via an anterior interbody spinal surgical technique. Each animal was positioned supine. A standard anterior approach was then used to expose the lumbar spine. A midline incision was made from the umbilicus toward the symphysis pubis. Dissection was carried down through the skin and subcutaneous tissue to expose the midline raphe, which was then incised to enter the abdomen through a transperitoneal approach. Bowel contents were retracted and packed cephalad to protect the bowel and maintain position out of the exposed operative field. At this point, the posterior peritoneal sheath was incised and the great vessels noted. The aorta, vena cava and bifurcation of the left and right common iliac vessels were dissected for free mobility overlying the spine. Middle sacral artery and venous branch were ligated. The vessels were retracted with blunt retractors to allow direct approach to the ventral aspect of the lumbar spine. When the disc space $L_{5-6}$ was identified, a marker probe was placed in position and a lateral x-ray was obtained to confirm the appropriate level of disc. After confirmation of level, the probe was removed and a complete discectomy was performed. The anterior longitudinal ligament was cut away as well as anterior annulus material. The disc was then removed in total.

The bony endplates were cleaned and penetrated so that there was vascular blood flow across the endplate. To facilitate placement of the implants, the disc space was distracted using a distracter instrument. Two bioactive spinal implants were placed into the distracted disc space, and carefully impacted. A calcium phosphate/bone marrow aspirate (BMA) bone graft material was packed around and between the implants in the disc space.

The dynamic DOC™ Ventral Cervical Stabilization System (DePuy Acromed, Raynham, Mass.) was placed ventrally to prevent hyperextension of the motion segment and subsequent dislodgment or migration of the implant devices. Following placement, the vessels were allowed to return to their normal position. The posterior peritoneal sheath was then closed with running absorbable suture. The bowel content was allowed to go back into position followed by standard closure of the ventral abdominal wall, the midline fascia, and the skin with subcuticular absorbable suture material.

Radiographs were taken immediately post-operative to verify implant placement and serve as baseline for comparison.

Figure 7:
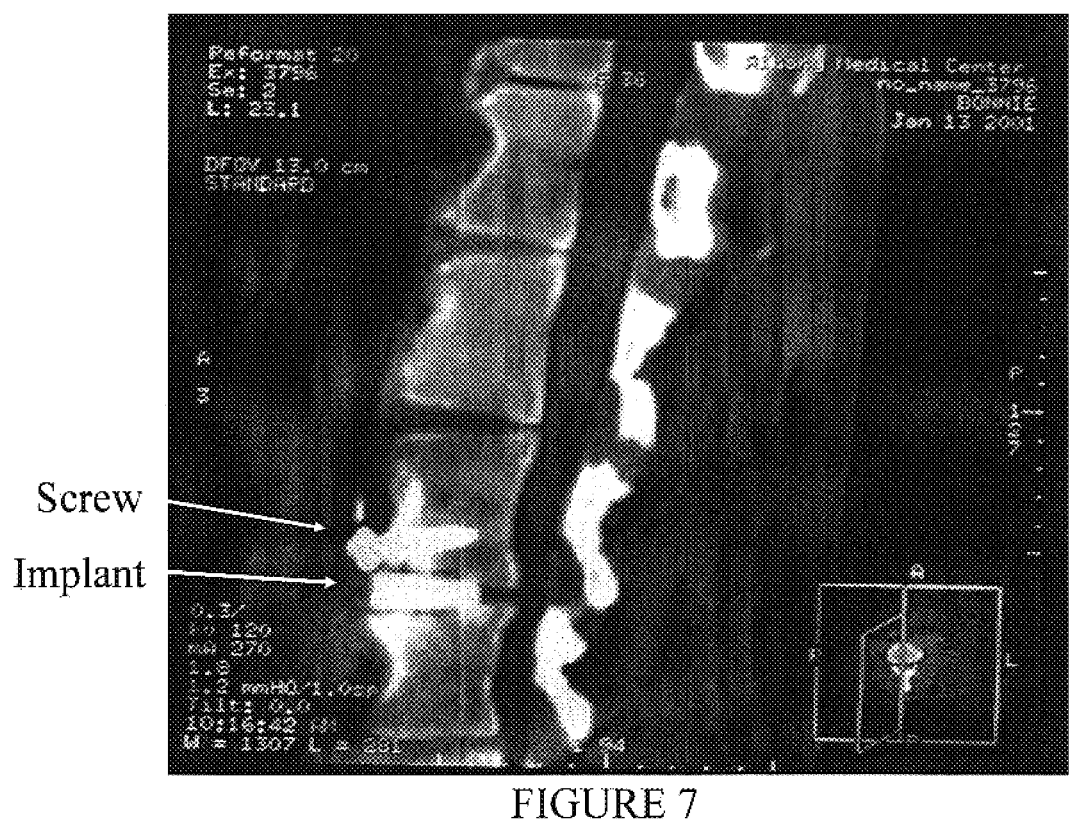
FIG. 7 provides a cat-scan (CT) image of the implant of the present invention implanted in a non-human primate model at 4 weeks.
Figure 8:
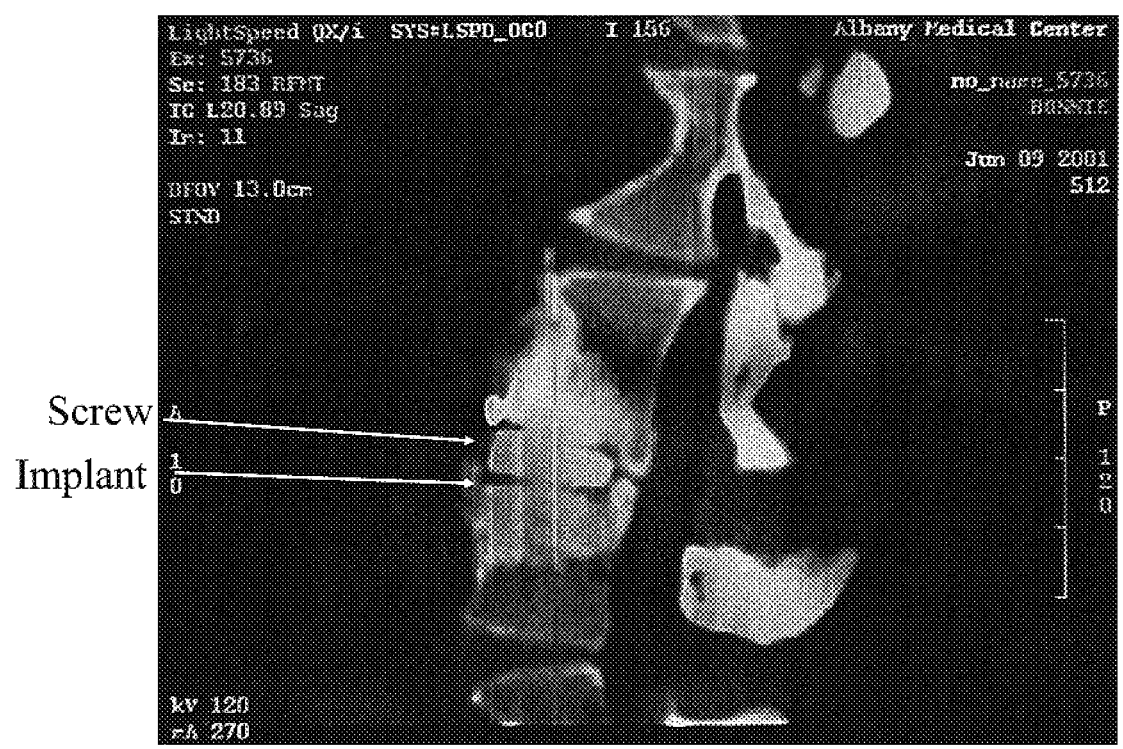
FIG. 8 provides a CT image of the implant of the present invention implanted in a non-human primate model at 6 weeks.

The rate and quality of healing were assessed using radiographs and CT scans taken at 1, 2, 3, and 6 months (FIGS. 7 & 8).

At six months post-operatively, animals were anesthetized (induction by ketamine (10–15 mg/kg BW IM), and, at the discretion of the attending veterinarian, diazepam (10 mg, IM) or acepromazine (1.0 mg/kg, IM) and then euthanized. Following euthanasia, the lumbar spine was retrieved en bloc and the specimens were photographed and observed grossly.

Immediately after sectioning, the excised spinal specimens were inspected for successful fusion and structural integrity of each motion segment. The DOC™ system was removed and the cranial segments were separated from the caudal segments and the specimens photographed and observed grossly.

Specimens without sufficient structural integrity for mechanical testing were immediately prepared for histologic evaluation. Those with sufficient structural integrity were mechanical tested and then prepared for histological evaluation.

All procedures were performed in accordance with Albany Medical College's Internal Animal Care and Use Committee and Quality Assurance Unit.

Results

Figure 9A:
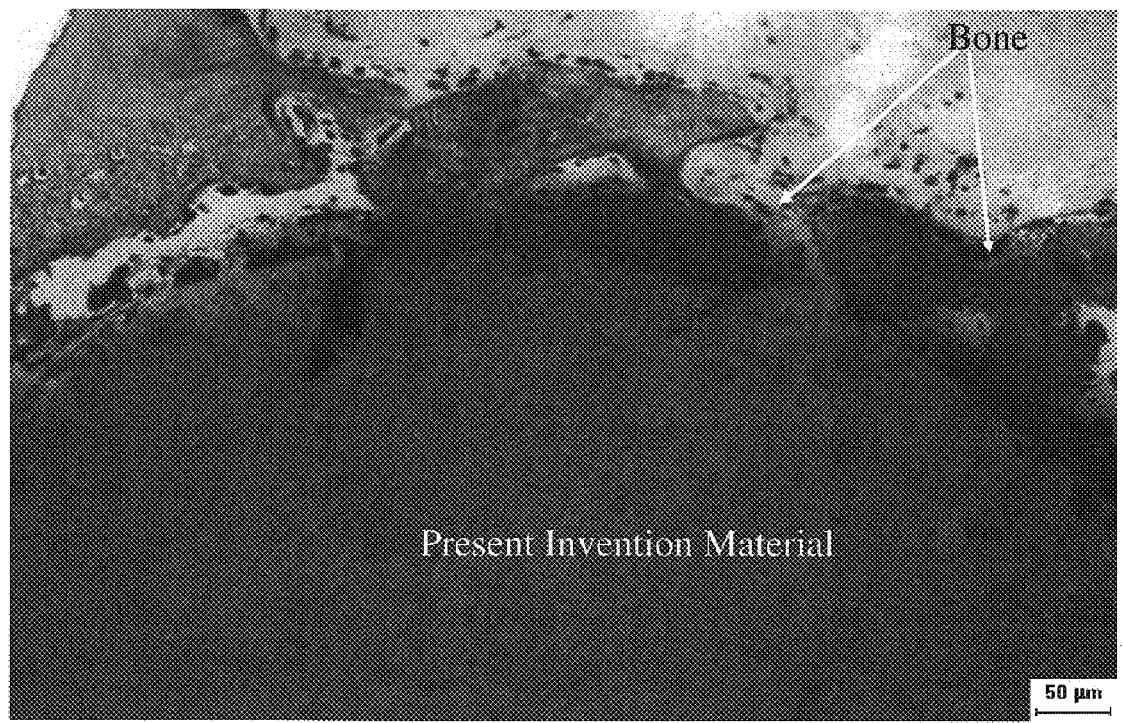
FIGS. 9a and 9b provide histological images of the implant of the present invention implanted in a non-human primate model.
Figure 9B:
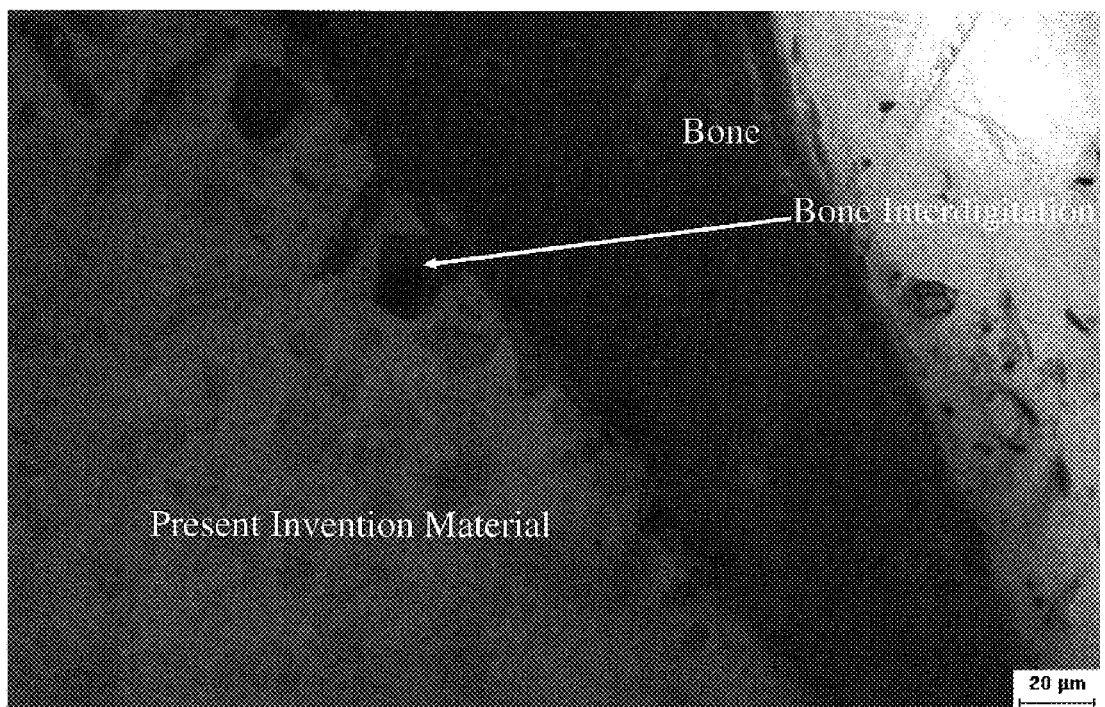

Bridging bone was found around the implants in all cases (FIGS. 9a and 9b). In all cases, the non-destructive flexion testing supported the presence of fusion. There were no Rhakoss particulates noted, and there were no signs of adverse response to the implants. In fact, minimal scar tissue was observed.

Example 10

Manufacture of Spinal Implants

A resin blend (about 20% to about 50% of total implant composition) of DUDMA, TEGDMA, initiator and stabilizer were poured into a Ross planetary mixing system (Hauppauge, N.Y.). The mixer was sealed, mixing was commenced and a vacuum was applied for approximately 15 minutes to about 30 minutes. After the mixer was turned off and the vacuum released, one or more fillers (about 15% to about 80% of the total implant composition) such as E-glass fibers, borosilicate fillers, silica fillers, and combeite fillers were added. Mixing was commenced and a vacuum was drawn for approximately 15 minutes to about 30 minutes upon the addition of each increment of filler. Once all of the fillers were incorporated into the resin, a vacuum was drawn for an additional 20 minutes. The mixture was then agitated on a vibrating table with vacuum for about 5 minutes to 60 minutes. The material was extruded into a mold cavity for molding into various bulk geometries.

The mold cavities were heated in a Despatch LFD Series oven and cured at about 40° C. to about 180° C. for a time duration of about 1 hour to 20 hours to form a molded body. Various shaped bodies or implant bodies were then formed.

The materials can also be hot extruded, injection molded, compression molded, or reacted in a mold with a catalyst other than heat.

The cylindrical stock was machined at MedSource (Laconia, N.H.) into spinal implants of the various shapes disclosed herein, having a generally anatomical shape with convex superior and inferior surfaces, lordotic angles, and the like.

Those skilled in the art will appreciate that numerous changes and modifications can be made to the many embodiments of the invention and that such changes and modifications can be made without departing from the spirit of the invention. It is therefore intended that the appended claims cover all such equivalent variations as falling within the true spirit and scope of the invention.

What is claimed is:

1. An implant comprising a synthetic, bioactive spinal implant material formed from a one-paste, 0% by weight bisphenol-A-glycidyl methacrylate polymerized resin matrix comprising about 10% by weight to about 60% by weight of the total composition of the implant material, the polymerized resin matrix comprising diurethane dimethacrylate and tri-ethylene glycol dimethacrylate resins, the resin matrix further comprising silane treated borosilicate filler, the implant material having a range of radiopacity from about 30 to about 55 and a range of stiffness from about 6 GPa to about 20 GPa.

2. The implant of claim 1 wherein said filler is bioactive.

3. The implant of claim 2 wherein said filler comprises combeite.

4. The implant of claim 1 wherein the polymerized resin matrix comprises about 20% by weight to about 40% by weight of the total composition of the implant material.

5. The implant of claim 2 wherein there is about 60% by weight to about 80% by weight filler comprising the total composition of the implant material.

6. The implant of claim 1 having a range of radiopacity from about 38 to about 50 and a stiffness from about 8 GPa to about 17 GPa.

7. A synthetic spinal implant material comprising 0% by weight bisphenol-A-glycidyl methacrylate, polymerizable resin matrix comprising at least diurethane dimethacrylate and tri-ethylene glycol dimethacrylate resins and silane treated borosilicate filler, said material, when polymerized, exhibiting a radiopacity from about 30 to about 55 and a stiffness of about 6 GPa to about 20 GPa.

8. The synthetic spinal implant material of claim 7 wherein the polymerizable resin matrix comprises about 10% by weight to about 90% by weight of the total composition of the implant material.

9. The synthetic spinal implant material of claim 7 wherein the polymerizable resin matrix comprises about 20% by weight to about 40% by weight of the total composition of the implant material.

10. The synthetic spinal implant material of claim 7 wherein said filler comprises about 60% to about 80% of the total composition of the implant material.

11. The synthetic spinal implant material of claim 7 further comprising combeite.

12. A method of making a one paste synthetic spinal implant material having 0% by weight bisphenol-A-glycidyl methacrylate, comprising:
providing a blend of diurethane dimethacrylate and tri-ethylene glycol dimethacrylate;
mixing said blend with at least one filler comprising silane treated borosilicate comprising from about 22% by weight to about 24% by weight of the material, the blend of diurethane dimethacrylate and tri-ethylene glycol dimethacrylate comprising from about 30% by weight to about 40% by weight of the material; and
agitating the resultant mixture to form said implant material having, when polymerized, a radiopacity from about 30 to about 55 and a stiffness of about 6 GPa to about 20 GPa.

13. The method of claim 12 further comprising combeite.

14. The method of claim 12 wherein the filler comprises about 60% by weight to about 80% by weight of the total composition of the implant material.

15. The method of claim 12 wherein the material has a range of radiopacity of about 38 to about 50 and a range of stiffness from about 8 GPa to about 17 GPa.

16. A synthetic, bioactive spinal implant material formed from a one-paste, 0% by weight bisphenol-A-glycidyl methacrylate polymerized resin matrix comprising about 24-percent to about 28 percent by weight diurethane dimethacrylate and about 7 percent to about 9 percent by weight and tri-ethylene glycol dimethacrylate resins, about 22 percent to about 24 percent by weight silane treated borosilicate filler, and said material having a range of radiopacity from about 30 to about 55 and a range of stiffness from about 6 GPa to about 20 GPa.

17. The synthetic spinal implant material of claim 7 comprising 22% to 24% by weight of silane treated borosilicate.

18. The spinal implant material of claim 7 comprising 24% to about 28% by weight diurethane dimethacrylate and 7% to about 9% by weight tri-ethylene glycol dimethacrylate.

19. The spinal material of claim 7 comprising a one-paste system.

20. The spinal material of claim 7 having a radiopacity between about 38 to about 50 and a range of stiffness from about 8 GPa to about 17 GPa.

21. The spinal material of claim 7 wherein said polymerized material forms calcium phosphate on its surface when contacted with bodily fluid.

* * * * *

UNITED STATES PATENT AND TRADEMARK OFFICE
CERTIFICATE OF CORRECTION

| | | |
|---|---|---|
| PATENT NO. | : 6,987,136 B2 | Page 1 of 1 |
| APPLICATION NO. | : 10/127947 | |
| DATED | : January 17, 2006 | |
| INVENTOR(S) | : Erik M. Erbe et al. | |

It is certified that error appears in the above-identified patent and that said Letters Patent is hereby corrected as shown below:

Column 4,
Line 10, delete "the to" and insert -- the resultant mixture to --.

Signed and Sealed this

Twenty-seventh Day of June, 2006

JON W. DUDAS
*Director of the United States Patent and Trademark Office*